United States Patent
Descales et al.

[11] Patent Number: 5,861,228
[45] Date of Patent: Jan. 19, 1999

[54] CRACKING PROPERTY DETERMINATION

[75] Inventors: Bernard Descales, Marseilles; Claude Granzotto, Pelissanne; Didier Lambert, Saint-Mitre-Les-Remparts; Jean-Richard Llinas, Marseilles; Andre Martens, Chateauneuf-Les-Martigues, all of France

[73] Assignees: BP Chemicals Limited; Naphtachimie S.A.

[21] Appl. No.: 466,594

[22] Filed: Jun. 6, 1995

[30] Foreign Application Priority Data

Oct. 7, 1994 [GB] United Kingdom ............... 9443001l

[51] Int. Cl.⁶ .................................................. G06F 15/46
[52] U.S. Cl. .................. 436/171; 364/498; 364/554; 422/62; 422/82.05; 436/50; 436/52; 436/55; 436/60; 436/139; 436/140; 436/141; 436/142; 436/143; 436/164; 436/183
[58] Field of Search ............................ 364/554, 571.01, 364/571.04, 498; 585/501, 613; 422/62, 82.05; 436/50, 52, 55, 60, 139–143, 164, 171, 183

[56] References Cited

U.S. PATENT DOCUMENTS

| | | |
|---|---|---|
| 3,896,312 | 7/1975 | Brown et al. ............................ 250/343 |
| 3,997,786 | 12/1976 | Lauer et al. . |
| 4,251,870 | 2/1981 | Jaffe . |
| 4,766,551 | 8/1988 | Begley . |
| 4,882,755 | 11/1989 | Yamada et al. . |
| 5,023,804 | 6/1991 | Hoult . |
| 5,082,985 | 1/1992 | Crouzet et al. ......................... 585/501 |
| 5,121,337 | 6/1992 | Brown . |
| 5,153,140 | 10/1992 | Langfeld et al. . |
| 5,225,679 | 7/1993 | Clarke et al. ............................ 250/343 |
| 5,311,445 | 5/1994 | White . |
| 5,361,912 | 11/1994 | Krieg et al. . |
| 5,446,681 | 8/1995 | Gethner et al. ......................... 364/554 |
| 5,452,232 | 9/1995 | Espinosa et al. ....................... 364/498 |
| 5,475,612 | 12/1995 | Espinosa et al. ....................... 364/500 |

FOREIGN PATENT DOCUMENTS

| | | |
|---|---|---|
| 305090 | 3/1989 | European Pat. Off. . |
| 345182 | 12/1989 | European Pat. Off. . |
| 437829 | 7/1991 | European Pat. Off. . |
| 607048 | 7/1994 | European Pat. Off. . |
| 625702 | 11/1994 | European Pat. Off. . |
| 631810 | 1/1995 | European Pat. Off. . |
| 2626579 | 8/1989 | France . |
| 94/08226 | 4/1994 | WIPO . |

OTHER PUBLICATIONS

"Near–Infrared Spectrum Qualification via Mahalanobis Distance Determination" (*Applied Spectroscopy*; vol. 41; No. 7; R. G. Whitfield et al. pp. 1204–1213; ©1987.

"Unique Sample Selection via Near–Infrared Spectral Subtraction" (*Analytical Chemistry*; vol. 57; No. 12; D. E. Honigs et al.; pp. 2299–2303 ©1985.

"Selection of Calibration Samples for Near–Infrared Spectrometry by Factor Analysis of Spectra" (*Analytical Chemistry*; vol. 60, No. 6; G. Puchwein; pp. 569–573; ©1988.

(List continued on next page.)

*Primary Examiner*—Arlen Soderquist
*Attorney, Agent, or Firm*—Fay, Sharpe, Beall, Fagan, Minnich & McKee

[57] ABSTRACT

An apparatus for on-line measuring physical property data of hydrocarbon products such as octane number, cetane number, density, vapour pressure and the like or gasoline/alcohol ratio, comprising means for providing (N)IR radiation in a predetermined spectral range; means for transmitting light at selected wavelengths in the (N)IR spectral region; means for delivering light from said transmitting means to a hydrocarbon product line; means for allowing an optical path length in the hydrocarbon product line; means for detecting the light transmitted through the said optical path; means for providing the obtained signal to be input to processing equipment for spectral analysis and correlating the spectral data to the physical property data of hydrocarbon products such as octane number, cetane number, density, vapour pressure and the like or gasoline/alcohol ratio.

35 Claims, 1 Drawing Sheet

OTHER PUBLICATIONS

"Selection of Samples for Calibration in Near–Infrared Spectroscopy. Part II: Selection Based on Spectral Measurements" (*Applied Spectroscopy*: vol. 44, No. 7; T. Isaksson and T. Naes; pp. 1152–1158; ©1990.

"The Design of Calibration in Near Infra–Red Reflectance Analysis by Clustering" (*Journal of Chemometrics*; vol. 1; T. Naes; pp. 121–126 ©1987).

"Nonlinear Multicomponent Analysis by Infrared Spectrophotometry"; *Analytical Chemistry*; vol. 55; M. Maris and C. Brown; pp. 1624–1702; ©1983.

"Multicomponent Analysis of FT–IR Spectra"; *Applied Spectroscopy;* vol. 45, No. 6; P. Saarinen and J. Kauppinen; pp. 953–963; ©1991.

O. U. Anders *Anal. Chem.* 1972, 44, 1930–1933.

C.W. Brown et al. *Anal. Chem.* 1976, 48, 191–195.

A.J. Martens et al. *Hydrocarb. Proc.* 1979, Apr., 199–202.

J.J. Royer *Sci. Terre, Ser.: Inf. Geol.* 1984, 20, 223–243.

H.A.M. Rasheed et al. *J. Pet. Res.* 1986, 5, 1–17.

M.A. Puskar et al. *Anal. Chem.* 1986, 56, 1981–1989.

H.A.M. Rashid et al. *J. Pet. Res.* 1988, 7, 169–179.

B. Descales et al. *Pet. Tech* 1989, 349, 2–8.

H.A. Rashid et al. *Fuel Sci. Technol. Int.* 1989, 7, 237–250.

A. Martens et al. *Int. Conf. Near Infrared Spectrosc.* 1991, 447–481.

S. Kokot et al. *Proc. SPIE—Int. Soc. Opt. Eng.* 1992, 1575, 495–496.

J.M. McDonald et al. *NPRA Computer Conf.* 1992, Paper N. CC–92–137.

S.J. Swarin et al. *Spectroscopy* 1992, 7, 42–49.

B. Descales et al. *Analysis* 1993, 23, M25–M28.

I. Cermelli et al. in "Near Infrared Spectroscopy" Harwood: New York, 1992, pp. 395–400.

S.M. Maggard et al, *Proc.–Annu. Symp. Instrum. Process Ind.* 1993, 48, 61–67.

J. Workman. *J. Near Infrared Spectrosc.* 1993, 1, 221–245.

J. Coates *Hydrocarb. Technol. Int.* 1994, 193–197.

T. Zerlia *Riv. Combust.* 1994, 48, 349–354.

Y. Yamamoto et al. *Idemitsu Gino* 1994, 37, 608–615.

D. Lambert et al. *Hydrocard. Process,* 1995, 103–108.

R. C. Fox *Anal. Chem.* 1976, 48, 717–721.

V. C. Utterback *Chem. Engineer.* 1976, 83, 141–144.

A. Espinosa et al. *Oil Gas J.* 1994, 92, 49–56.

CRACKING PROPERTY DETERMINATION

This invention relates to a method of determining or predicting by near infra red (NIR) spectroscopy properties of feeds or products and/or yields in steam cracking processes in particular involving hydrocarbons, especially in hydrocarbon refineries NIR spectroscopy has many advantages over other methods of analysis in refineries and can cover a large number of repetitive applications accurately, quickly and on line. The NIR region between 800 and 2500 nm contains the totality of molecular information in the form of combinations and overtones from polyatomic vibrations, but Mathematical techniques are needed to exploit this information and to calculate the desired parameters. U.S. Pat. No. 5,490,085 (issued Feb. 6, 1996), U.S. Pat. No. 5,452,232 (issued Sep. 19, 1995), U.S. Pat. No. 5,475,612 (issued Dec. 12, 1995), and U.S. Pat. No. 5,082,985 (issued Jan. 21, 1992) the disclosure of which is hereby incorporated by reference, describe respectively the use of NIR for determining octane number, yields and/or properties of a product of a chemical process or separation process from analysis on the feeds to that process, and yields and/or properties of a product of a blending operation again from analysis on the feed thereto and for determining at least one condition of operation of the steam cracking reaction.

At present, numerical methods described for modelling physicochemical properties based on NIR spectra all are of a correlative nature and involve relations of a regressional character between the property(ies) studied. Among these multivariable analyses are multilinear regression (MLR), Principle Component Regression (PLR), Canonic regression, and regression by Partial Least Squares (PLS). In all cases there is sought between the property and the NIR spectrum a relation which may be linear but is usually quadratic or of higher algebraic form involving regression coefficients applied to each absorption. The establishment of any regression requires a progressive calibration, as the approach is empirical and not supported by a theory.

These techniques have disadvantages, the chief of which is the need for establishing a strong correlation between the spectrum and the property, and their difficulty in dealing with positive or negative synergy between components contributing to that property. Furthermore there are practical difficulties mainly in the need to identify sample families having the same kind of relation between the spectra and the properties to be modelled. Thus the model may be limited especially with a non linear relation between spectrum and property. Especially when at the edges of the available data the accuracy of the model diminishes. The stability of the model is also a problem, as is the need when adding new standards to do laborious revisions to give the new model, especially when adjusting to a new feedstock for a process; thus testing the yields on 4 products leaving a steam cracker requires 4 models, each of which has to be changed for each change of the feed not included in the calibration.

We have discovered a new approach avoiding the above problems with correlations, and regression calculations, and being capable of being expanded automatically with use of a new feed of different quality.

The present invention provides a method of determining or predicting a value Px, of a property of a feed to a steam cracking process or yield of said process which method comprises measuring the absorption $D_i$x of said feed at more than one wavelength in the region 600–2600 nm, comparing the said absorptions or a derivative thereof with absorptions $D_i$m or derivatives thereof at the same wavelengths for a number of standards S in a bank for which the said property or yield P is known, and choosing from the bank at least one, and preferably at least 2 standard(s) $S_m$ with properties or yields $P_m$ said standard $S_m$ having the smallest average values of the absolute difference at each wavelength i between the absorption $D_i$x (or derivative thereof) for the feed and the absorption $D_i$m (or derivative thereof) for the standard $S_m$ to obtain value $P_x$ and with averaging of said properties or yields Pm when more than 1 standard $S_m$ is chosen The above method can be performed without regression or correlation techniques.

Thus for the performance of the method of the invention, a bank is prepared in which the NIR spectra are recorded at many wavelengths for a large number of standard materials, together with their properties determined by alternative techniques e.g. gaschromatography for chemical compositions or yields determined by known methods. The standards are chosen to cover the area in which the method is to be used, so for determination of the yield of ethylene, a range of feeds to the steam cracker is chosen and under constant cracking conditions eg temperature pressure and catalyst the yield of ethylene is measured. The number of wavelengths chosen may be 2–1000 e.g. 5–200 or 20–90 such as 60–80 while the number of standards can be at least 100 or 1000, or 100,000 up to 5 million depending on property(ies) chosen.

The wavelengths chosen may be at regular intervals such as each 1–50 or 15–35 nm, (or each 1–5 nm or each nanometer) or may be at irregular intervals e.g. with intervals of 1–100 nm, e.g. 1–50 especially 1–35 nm which may be random or chosen because of a change in the shape of the spectral curve at that wavelength e.g. a peak, trough or shoulder. The wavelengths may be in the region 600–2600 nm, eg 1000–2500 nm but preferably 1500–2600 such as 2000–2550 nm while the wavenumbers may be 16,600–3840 $cm^{-1}$, e.g. 10000–4000 $cm^{-1}$, 6660–3840, or 5000–3900 $cm^{-1}$ Frequencies in Hertz are obtained by multiplying the wavenumbers by $3 \times 10^{10}$ cm/sec.

The absorptions for the unknown sample are compared with the absorptions at the same wavelength of the standards, and those standards chosen having the smallest differences. The properties of those chosen standards are then averaged to determine the property or yield of the unknown sample. The absorptions at more than one wavelength may be chosen, e.g. 2–1000 such as 5–100 or 10–20.

In the method of the invention the standards chosen are those with the smallest average values of the absolute difference at each wavelength i between the absorption/optical density (or a derivative thereof) $D_{ix}$ for the unknown material and the corresponding absorption/optical density (or derivative thereof) $D_{im}$ for the standard. The averages may be in respect of the mean value of $D_{ix}-D_{im}$, (whatever its sign ie the absolute differences), or $(D_{ix}-D_{im})^2$ and may be the simple mean value or the differences may be weighted to take account of the different sensitivity of the absorption to the property at that wavelength or the different sensitivity of the spectrometer at that wavelength. For each standard in the bank of standards for the type of material in question, the average difference is found as described and the standards with the smallest average differences chosen, e.g. at least 1 but preferably at least 2 such as up to 1000 smallest such as 1 (or 2) to 100 or 1 (or 2) –20 but in particular 1 (or 2) –10 and especially 2–6 smallest. Advantageously the average differences chosen and hence the standard (or standards $S_m$) chosen for the property or yield wanted are such that in relation to the unknown material X and each chosen standard $S_m$ the following function is met $i_{xm}/\Sigma D_{ix}$ < experimental error wherein $i_{xm}$ is the proximity index and is defined by $i^2(_{xm})=\Sigma(D_{ix}-D_{im})^2$ and the experimental error is in determining said property or yield in the standard. The value $P_x$ of the property or yield is the same as $P_m$ or the average of Pm when more than one standard $S_m$ is chosen.

In order to aid the choice of the appropriate standards, especially in relation to a large number of wavelengths for a complex unknown mixture, it is preferred to limit the choice to those defined by means of a minimal index. For the chosen standard the minimal index is at least the same as the differences between the absorptions of the unknown and the standards. Mathematically, this may be expressed as $i^2ab \leq i^2M$ where iM is the minimal index for the property, and iab is a measure of the deviation (called the proximity index) at all the chosen wavelengths between absorption of the unknown and a chosen standard b. That measure is defined by $$i(ab)^2=\Sigma_i(D_{ia}-D_{ib})^2 \qquad (1)$$

where $D_{ia}$ is the optical density (or absorbence) of unknown a at wavelength i (or a derivative thereof e.g. a first, second or third derivative of that density); and $D_{ib}$ is the optical density (or absorbence) of standard b at that wavelength i (or a derivative thereof e.g. a first, second or third derivative of that density). The value of $D_1$ is the optical density or the optical density difference with respect to the baseline of the spectrum at that wavelength, or the baseline interpolated between 2 wavelengths on either side thereof.

If desired instead of the optical density $D_i$ a normalized density $W_i$ may be used where $W_i=D_i/\Sigma D_i$. This normalization avoids errors due to small electronic fluctuations in the apparatus and compensates for small differences in the optical path between the optical cells.. In this case the proximity index is defined by $$I(ab)^2=\Sigma_i(W_{ia}-W_{ib})^2 \qquad (2)$$

The indices can be weighted as desired for increased resolution. One approach is to define the indices as follows.

$$I(ab)^m=\Sigma Abs.\,val.(X_{ia}-X_{ib})^m/\sigma i^n \qquad (3)$$

where $X_i$ is $D_i$ or $W_i$ or a mathematical combination thereof, $\sigma_i$ is the standard deviation of X for the set of samples considered (at that wavelength) and each of m and n, which are the same different is the weighting factor which is positive but can be a whole number or a fraction. Other variants can be used with other weighting factors such as those involving the spectral experimental error $e_i$, where $e_i$ is the reproducibility of the spectral measurement at wavelength i. The choice between the different options for the weighted indices may be dictated by numerical efficiency.

The reproducibility of the experimental measurements in the standards may be at least 90% or 94% or 95%. The minimal index may be obtained from a reference standard samples set according to the following procedure, hereafter called the Minimal Index Procedure. The NIR spectra for the standard samples A and B and their property P e.g. density are determined. By means of equation (1), (2) or (3), the value of the proximity index iab is determined via the absorptions at a series of wavelengths; this index is applicable to the difference in properties $P_a-P_b$ called $EP_{ab}$. This process is repeated with other pairs of standards c and d, e and f etc to obtain a series of Proximity Indices $i_{cd}$ etc with corresponding property differences $EP_{cd}$ etc. For different values of a parameter L which is greater than the indices $i_{ab}$ etc, the corresponding values of $EP_{ab}$ etc are averaged to give an average $EP_{ij}$ for that value of L; the different values of $EP_{ij}+t\sigma/\sqrt{K}$ are then plotted on a graph against L. $\sigma$ is the accuracy of the property determination and K is the number of pairs of samples for which i is inferior to a given L. t is the Student factor at a given level of confidence. The intercept is then measured between the curve obtained and a line usually horizontal which is the reproducibility of the property level at an appropriate confidence interval e.g. 90% or more usually 95%; The portion of the intercept gives the minimal index $i_{min}$, which is the minimum value of $i_{ab}$ for which $P_a=P_b$ within the frame of experimental error.

From this minimal index by Procedure 1, the standards can be chosen which have values of $i^2ab \leq i^2_{min}$, where in this case a is the unknown and b is a standard, as in this case the difference between Property a and Property b is less than or equal to $\sigma\sqrt{2}$, where $\sigma$ is the experimental error in measuring the property. Then from the property P values of the chosen standards, the property of the unknown is obtained by averaging those values, usually the arithmetic mean, but optionally with weighting.

The method of the invention may be used to determine more than one Property P at once, e.g. at least 2, such as 1–30 e.g. 2–10 properties at once. Each property of the standards has a particular minimal index, which may lie in the region $0–10^{-10}$ eg $10^{-2}$ to $10^{-8}$, in particular $5\times10^{-7}$ to $5\times10^{-4}$. If the Minimal Index chosen is the smallest for all the properties desired, then the same one may be used for all the properties and the standards chosen will be suitable for all the properties. The Minimal Index for each property may be used separately, with different numbers of standards chosen for each property (assuming different Minimal Indices). If desired the same Minimal Index may be used, which is not the smallest, resulting in some of the chosen standards (with less than their Minimal Index) giving some properties of high accuracy and some (with a higher Minimal Index) giving properties of less high accuracy.

The property to be determined may be of the sample being analyzed or the yield of a product obtained from that sample i.e. a product of cracking the sample, as the property value obtained is derived from the standards, and they will have been determined as needed for the eventual use. U.S. Pat. No. 5,452,232, U.S. Pat. No. 5,475,612, and U.S. Pat. No. 5,082,985 referred to above describe such techniques when applied to use of NIR with correlation to blending or cracking operation; the same principles apply in the present method.

If the density of the standards in the bank is sufficient to have $i^2_{ab} \leq i^2_{min}$ as is usually the case, the above procedure is very satisfactory. But there are occasions when the bank is incomplete, because of shortage of data of properties in a particular area i.e. a low density of standards or the sensitivity of the property to changes in absorption is so small, that a very small Minimal Index is required and there may be few standards with proximity indices meeting it. It is possible simply to use a larger Minimal Index with e.g. 1–5 times such as 1.5–2 times the Minimal Index; the results may be less accurate than those from a smaller Minimal Index.

However, a more accurate approach with a low density of standards involves a special densification process of Procedure 2, in which random or semi random densification of the neighbourhood of the unknown is achieved by generation of synthetic standards, based on standards already in the bank. Each new synthetic standards may be obtained from combinations of standards taken at random from the bank but preferably it is obtained from the other standards by the constraint of choosing only a mixture of N standards for which $$(Min)C_j - u_j \leq C_j \leq (Max)C_j + u_j \qquad (4)$$

$$\text{and } \Sigma C_{ij} = 1 \qquad (5)$$

where $C_j$ is the fraction of component j in the sample $_i$.

Min $C_j$ is the minimum amount of $_j$ in the initial industrial calibration covering the correct area of $_j$ in the industrial mixture, or in the samples for which the method is to be used.

Max $C_j$ is the maximum amount of $_j$ in the initial industrial calibration covering the correct area of $_j$ in the industrial mixture or in the samples for which the method is to be used.

uj is usually between 1 and 0.01 preferably between 0.5 and 0.1 and can be fixed for each property.

The constraints over the choice of such mixtures of N standards can also be equally fixed in the spectral area from which the samples will be drawn in order to remain in the areas of similar chemical nature.

The number of samples effectively drawn into the bank in this densification can be of several thousand generally 1000–2000. The calculation time is extended without significant deterioration in the results. If no further neighbours are found, the trawl of new samples drawn in is enlarged.

The spectrum of each mixture is calculated by the combination of the spectra of the standards used according to the formula $$S_{Mi} = \Sigma C_{ij} \times S_j \qquad (6)$$

where $S_j$ is the spectrum in the mixture of component $_j$ in the calibration matrix.

The properties of each mixture PMi can be calculated by a generally linear combination of the properties of the standards according to the formula $$P_{Mi} = \Sigma C_{ij} \times P_j \qquad (7)$$

where $P_j$ is the property of component j

In the case of non linear additive properties, appropriate mixing factors can be applied e.g. by blending factors or similar for density and viscosity.

Having obtained the spectrum and the properties of the synthetic mixtures, these can be used as "standards" to help determine the properties of an unknown sample in the same way as a conventional standard.

Instead of using either of the two above approaches, 1–7, a third type Procedure 3 may be used as follows. The Q nearest samples to unknown X can be found from a selection from the bank samples for which the proximity index to the unknown sample is $(V) \times i_{min}$) where v is 0.1<v<10, (8) preferably 0.5<v<2 or $1 \leq v \leq 5$. Then by the method of least squares is found a generally linear combination of the standard products which are (the Q nearest samples to reproduce the spectrum of X according to the equation.

$$S_x = \Sigma C_R \times S_r \qquad (9)$$

where $C_r$ is the coefficient for sample R in the total Q and $S_R$ is the spectrum of sample R. The coefficient $C_R$ which can be normalized to $C_R = 1$ or not and/or optimized by the least squares route, allows an estimation of the property $P_x$ according to the equation.

$$P_x = \Sigma C_R \times P_R \qquad (10)$$

where $P_R$ is the property of sample R.

The eventual size of the estimation error can be derived by application of Gaussian theory, also called the propagation error (see Eq.10).

The above third approach can only be applied if the product X is situated inside the maximum extension of the standard products defined by equation (8). If this is not the case, X is outside the field of the actual bank of products and escapes from the area of knowledge of the method into the area of learning.

The densification process described in relation to equations 4–7, or 9 or 10 is usually applied to the method of the invention involving no correlation or regression techniques. However, if desired the densification process may be applied to increase the number of "standards" for consideration in an NIR analytical technique involving the correlation or regression techniques as described above e.g. MLR. The present invention also provides a method for adding an extra synthetic standard to a bank of known standards, each of which relates at least one absorption in the 600–2600 nm region (or derivative thereof) of a feed to a steam cracking process to a known property related to that feed or yield of said process, which method comprises choosing from the bank at least 2 standards for which equations 4 and 5 above are met, considering mixing the chosen standards in at least one proportion to produce at least one mixture for use as a synthetic standard, and estimating the spectrum and property of said mixture according to equation 6 and 7 respectively.

The spectrum and property of each "mixture" can then be added to the bank and may be used to develop models through the known correlation/regression approach eg as described in U.S. Pat. No. 5,082,985.

The method of this invention is applicable to determination of the properties of feeds to a steam cracking, as well as the determination from the feed to the steam cracker of the potential yields of $C_2$–$C_6$ alkenes e.g. ethylene, propylene, butenes and a $C_5$ olefin fraction, or benzene in the steam cracking under standard conditions. Other "properties" of the feed which relate to its suitability for use in steam cracking under standard conditions may be measured such as its potential yield of methane and its cokability, ie the tendency to form coke in that cracking. Other properties of the feed that can be determined in addition include its chemical composition eg percentages of linear paraffinic hydrocarbons, isoparaffins, naphthenics compounds, aromatics and benzene, and its density and mean molecular weight. These parameters are important for the smooth operation of a steam cracker, as variations affect that operation, especially the olefin production. Such variations may result from changes intentional or otherwise in the feeds, which may be naphtha, condensates, liquefied gas and/or gas oil. The steam cracking may involve amounts of steam of 30–50% eg 40% (relative to hydrocarbon feed) riser inlet temperatures of 100°–400° C. eg 250° C. and riser outlet temperature of 800°–900° C. eg 830° C. and residence time of 0.1–5 sec eg 0.5 sec.

In each case the method may be applied to determine a property of the feed tested or yield from that feed preferably on line and especially with continous feed back from the results to control the production process.

In each of the above processes the property of a feed or yield determined or predicted by the method of the invention can be compared to the desired figure and notice taken of any deviations by adjusting the parameters of the cracking process e.g. proportion or nature of feed ie steam or hydrocarbon and/or temperature/pressure etc to bring the property back to the desired figure. This control of the cracking process, is usually performed with a micro computer which is linked to the spectrometer and also performs the search for the standards $S_m$. The inline control of the process is very efficient and very fast.

The present invention also provides an apparatus suitable for carrying out the method of the invention comprising an infra red spectrometer and a computer wherein the infra red spectrometer is linked to the computer program in such manner that the property may be determined continuously and in real time. The spectrometer is suitable for measuring spectra in the 600–2600 nm wavelength range and can be linked to a signal processing device to allow numerical treatment of the spectrum, preferably by Fourier transformation. The spectrometer receives at least one signal from a vessel containing feed or from a feed line. The information obtained can be used as an information vector for the computer which is programmed to determine the property or yield eg via calculations on the proximity indices in relation to standards. Conveniently in relation to a process, the computer may be used in a closed loop feedback control system for controlling processing equipment eg changing the process parameters in response to variations in the property and/or yield of product from the desired value, measurement of more than one absorption in the NIR spectrum of the feed.

The benefits of invention allow improvements in modelling with the following areas, identification and classification of novel feeds, simultaneous estimation of all of P properties on a sample without the need for generating P different models, and with the option of automatic upgrading of the model, the method being self learning or adjusting. The method of the invention overcomes the difficulties with the classical regressional approach, in particular avoiding all difficulties with numerical stability of the models, allowing easy and rapid identification and classification of a sample of a feed analyzed by spectral recognition and then instant conclusions as to whether the sample is known or unknown, allowing simultaneous determination of many properties.

The method also allows an extension of the field of application of the method without the need to rewrite the model, apart from the need to integrate the new samples which are inside or outside the previous field of validity of the method. This possibility of automatic learning, which is not possessed by traditional regression techniques, is a decisive advantage in the framework of continuous inline industrial control processes, because it allows the return of the industrial plant operations to the model in a certain and rapid manner in a minimum time and with all the properties considered in the model. In contrast classical regression methods would necessitate the redevelopment of all the models, which is long and laborious without being able to guarantee the result of the new model obtained, because a new validation period is necessary; in addition during the redevelopment of the model any commercial refinery use of the model is very limited. Furthermore, the method of invention allows equally the easy extension to a number of properties, which are simply incorporated into the known bank.

This remarkable possibility is true not only for conventional properties such as physical chemical and/or rheological properties, but also for complex ones. The methods of the invention equally allow application of the models from one apparatus to another and from one spectral region to another, where conventional regressive method cannot give satisfactory solutions. This apparatus portability is made possible by the fact that the distinctions between different spectra are the same in one apparatus as another, for the same type of spectrometer being considered (e.g. network scatter, Fourier transform, accousto optical system AOTS, diode etc). This portability between spectral region depends on the fact that as the spectral regions are intercorrelated, the relations between the spectra are maintained between one another.

The invention is illustrated in the following Examples in which the Minimal Index is calculated according to the Minimal Index Procedure described above. Mathematically the steps concerned are as follows.

For each couple of standard samples i, j, the Proximity Index $i_{ij}$ is determined from the NIR spectra by use of equation 1, 2, or 3 and the properties are measured. For each Proximity Index is calculated the absolute difference $EP_{ij}$ between the properties of the samples. The Minimal Index for property P is obtained from the average $EM_p(L)$ of $EP_{ij}$ for different values of L when L≧ij. Thus the $EM_p(L)=1/K$ $\Sigma \Sigma EP_{ij}$ for each of K samples for which ij ≦L.

$EMp(L)+t\sigma/\sqrt{K}$ is plotted against the proximity index and in addition there is plotted the reproducibility of the standard method at a given confidence level as defined in the Minimal Index Procedure above. The intercept of the curve from EMpL and the reproducibility give the upper limit i.e. the Minimal Index.

For the Examples the data is expressed in Tables in a form as shown below in which the data is as follows.

|  | Absorption | | | |
| --- | --- | --- | --- | --- |
|  | Weighting | Unknown | Estimated | Standard A | Standard B |
| Proximity Index | | | | |
| Wavelength λ | | | | |
| cm⁻¹       nm | | | | |
| Property 1 | | | | |
| Property j | | | | |
| Property m | | | | |

The wavelengths chosen are shown in columns 1 and 2.

Column 3 gives the weight loading associated with each wavelength for the proximity index for the standards; 1 denotes no loading.

Column 4 shows for the unknown sample the absorption at the various wavelengths and at the bottom the properties of that sample determined by standard methods.

Column 5 shows for the unknown sample the estimated values of the properties and the absorptions using the method of the invention based on the properties and absorptions of the chosen standards.

Columns 6, 7 etc show the values of the absorptions and properties for the standards chosen from the bank.

Line 2 give the value of the proximity index between the unknown sample and each of the chosen standards.

EXAMPLE 1

Determination of the properties of a mixture of hydrocarbons for feeding to a steam cracker and the yields of products therefrom.

The properties were sought of a mixture of hydrocarbons, a naphtha, a petroleum hydrocarbon cut which was a feed to a steam thermal cracker for producing olefins, such as ethylene, propylene and butenes, as well as cracked gasoline. The key properties of the feed are its density and its "potential content of ethylene", called CPC2, (ie yield of ethylene product) which is its capacity to product ethylene under standard steam cracking conditions. In addition, other important properties are its cokability Index (1C), which is the potential of the feed to generate coke [under the standard conditions of steam cracking] as well as the chemical composition eg the percentages of linear paraffinic hydrocarbon (LIN %), isoparaffins ISO %), naphthenics (NAPHT %) aromatics (ARO %) and benzene (BENZ %).

The NIR spectrum of a naphtha F on line to a steam cracker furnace was measured with a Fourier Transform spectrometer of 4800–400 $cm^{-1}$ (with baseline at 4720 $cm^{-1}$); the absorbances were normalized, but not weighted. The conditions of the steam cracking were % steam 40%, outlet temperature 830° C., residence time 0.5 sec. A bank of data on known naphthas with their NIR spectra and properties had been previously prepared, the properties being determined with respect to a steam cracking under the same standard conditions. By the Minimal Index Procedure and non weighting of the absorbances and Equation 2 the Minimal Index was determined as $3.7 \times 10^{-7}$. By the method of this invention the proximity indices between the unknown naphtha 1F and the bank of known naphthas were determined, and those known naphthas with proximity indices less than $3.7 \times 10^{-7}$ chosen. Five such naphthas were found, designated 1A–1E and the properties of naphtha 1F obtained by averaging those of 1A–1E. The Table 1.1 shows the absorbances for the napthas 1A–1F, as well as the estimated absorbances for 1F and the properties of 1A–1F, and the estimated properties of 1F. The table shows the accuracy of the method for the calculated properties, which are in agreement with the standard methods, any differences between the measured and estimated properties (columns 3 and 4) being within the limits of reproducibility of the reference methods.

Other properties of the naphtha, such as average molecular weight, may be obtained in a similar way.

EXAMPLE 2

The process of Example 1 was repeated with a different naphtha feed, whose analysis changed with time. The method was applied as in Ex 1 (with Minimal Index as in Ex.1).

The feed was analyzed on line with time and the potential yield of ethylene and the density monitored; the results are shown in the Table below. Other properties were measured once with the following results, potential yield of methane 14.55% and propylene 16.08% and 4 carbon olefins 9.86%, the coking index 87.21, mean molecular weight 88.68, and chemical composition 42.89% LIN, 34.60% of ISO, 17.62% NAP, 4.88% ARD and 1.79% of BEN

TABLE

| Time (mins) | 0 | 4 | 8 | 12 | 16 | 20 | 24 |
|---|---|---|---|---|---|---|---|
| CPC2 | 22.8 | 22.6 | 22.5 | 22.2 | 21.75 | 21.3 | 21.1 |
| Density kg/l | 685 | 687.5 | 689 | 672 | 694 | 697 | 700 |

TABLE 1.1

Determination of the properties of a mixture of hydrocarbons for feeding to a steam cracker

| Wavelengths λ (cm-1) | λ (nm) | 1F measured | Proximity Index 1F estimated 3,80E-08 | 1A 8,94E-08 | 1B 9,30E-08 | 1C 1,87E-07 | 1D 2,84E-07 | 1E 3,57E-07 |
|---|---|---|---|---|---|---|---|---|
| 4739 | 2110 | 0,000117 | 0,000114 | 0,000115 | 0,000111 | 0,000118 | 0,000111 | 0,000116 |
| 4726 | 2116 | 0,000146 | 0,0001466 | 0,000147 | 0,000142 | 0,000152 | 0,000144 | 0,000152 |
| 4717 | 2120 | 0,000185 | 0,0001866 | 0,000189 | 0,000178 | 0,000192 | 0,000188 | 0,000194 |
| 4673 | 2140 | 0,00066 | 0,0006506 | 0,00066 | 0,000628 | 0,000639 | 0,000605 | 0,000721 |
| 4669 | 2142 | 0,000677 | 0,000663 | 0,000667 | 0,000664 | 0,000653 | 0,000617 | 0,000735 |
| 4660 | 2146 | 0,000718 | 0,0007042 | 0,000711 | 0,000682 | 0,000691 | 0,000676 | 0,000777 |
| 4651 | 2150 | 0,000781 | 0,0007698 | 0,000775 | 0,000748 | 0,000756 | 0,000724 | 0,000846 |
| 4647 | 2152 | 0,000823 | 0,000811 | 0,000814 | 0,0007 9 | 0,000798 | 0,000764 | 0,000889 |
| 4643 | 2154 | 0,000868 | 0,000854 | 0,000859 | 0,000829 | 0,000843 | 0,000802 | 0,000937 |
| 4625 | 2162 | 0,00108 | 0,0010548 | 0,0010 | 0,0010 | 0,0010 | 0,0009 | 0,0011 |

TABLE 1.1-continued

Determination of the properties of a mixture of hydrocarbons for feeding to a steam cracker

| Wavelengths λ (cm-1) | Proximity Index Wavelengths λ (nm) | 1F measured | 1F estimated 3,80E-08 | 1A 8,94E-08 | 1B 9,30E-08 | 1C 1,87E-07 | 1D 2,84E-07 | 1E 3,57E-07 |
|---|---|---|---|---|---|---|---|---|
| 4621 | 2164 | 0,001112 | 0,0010928 | 0,001055 | 0,001022 | 0,001043 | 0,001009 | 0,001264 |
| 4613 | 2168 | 0,001145 | 0,0011332 | 0,001131 | 0,001101 | 0,001117 | 0,001072 | 0,001245 |
| 4604 | 2172 | 0,001184 | 0,001175 | 0,001177 | 0,001146 | 0,001155 | 0,001123 | 0,001274 |
| 4591 | 2178 | 0,001288 | 0,0012826 | 0,001289 | 0,001254 | 0,001269 | 0,001242 | 0,001359 |
| 4583 | 2182 | 0,001376 | 0,001366 | 0,00137 | 0,001343 | 0,001357 | 0,001325 | 0,001435 |
| 4550 | 2198 | 0,001962 | 0,0019714 | 0,001965 | 0,001952 | 0,001974 | 0,001951 | 0,002015 |
| 4537 | 2204 | 0,00223 | 0,002231 | 0,002223 | 0,002208 | 0,002235 | 0,002213 | 0,002276 |
| 4529 | 2208 | 0,002364 | 0,0023672 | 0,00236 | 0,002344 | 0,002372 | 0,002355 | 0,002401 |
| 4496 | 2224 | 0,002767 | 0,0027762 | 0,002765 | 0,002749 | 0,002777 | 0,002762 | 0,002828 |
| 4484 | 2230 | 0,003013 | 0,0030192 | 0,003005 | 0,002996 | 0,003026 | 0,003004 | 0,003065 |
| 4472 | 2236 | 0,003372 | 0,0033802 | 0,00337 | 0,003356 | 0,003385 | 0,003362 | 0,003428 |
| 4405 | 2270 | 0,015722 | 0,0157656 | 0,015732 | 0,015737 | 0,015831 | 0,015774 | 0,015754 |
| 4394 | 2276 | 0,017032 | 0,0170668 | 0,01706 | 0,017053 | 0,01707 | 0,01711 | 0,017051 |
| 4390 | 2278 | 0,017074 | 0,0171032 | 0,017113 | 0,017089 | 0,017089 | 0,017146 | 0,017079 |
| 4386 | 2280 | 0,017026 | 0,0170488 | 0,017072 | 0,017032 | 0,017035 | 0,017082 | 0,017023 |
| 4382 | 2282 | 0,016925 | 0,0169442 | 0,016977 | 0,01692 | 0,01692 | 0,016989 | 0,016915 |
| 4378 | 2284 | 0,016825 | 0,0168448 | 0,016882 | 0,016823 | 0,016815 | 0,016888 | 0,016816 |
| 4374 | 2286 | 0,016793 | 0,0168204 | 0,016862 | 0,016796 | 0,016788 | 0,016865 | 0,016791 |
| 4367 | 2290 | 0,017293 | 0,0173046 | 0,017329 | 0,017281 | 0,017284 | 0,017349 | 0,01728 |
| 4340 | 2304 | 0,026754 | 0,0267546 | 0,026706 | 0,026739 | 0,026904 | 0,026781 | 0,026643 |
| 4337 | 2306 | 0,027159 | 0,0272098 | 0,027144 | 0,027223 | 0,027335 | 0,027238 | 0,027109 |
| 4333 | 2308 | 0,026844 | 0,026879 | 0,026816 | 0,026912 | 0,026963 | 0,026899 | 0,026805 |
| 4329 | 2310 | 0,025944 | 0,0259448 | 0,025889 | 0,026002 | 0,025989 | 0,025933 | 0,025911 |
| 4318 | 2316 | 0,022338 | 0,0223474 | 0,022282 | 0,022401 | 0,022344 | 0,022343 | 0,022367 |
| 4303 | 2324 | 0,019545 | 0,0195754 | 0,019539 | 0,019589 | 0,019601 | 0,019574 | 0,019574 |
| 4292 | 2330 | 0,019333 | 0,0193696 | 0,019369 | 0,019367 | 0,019386 | 0,019408 | 0,019318 |
| 4281 | 2336 | 0,020823 | 0,0208396 | 0,020873 | 0,020841 | 0,02084 | 0,020909 | 0,020735 |
| 4274 | 2340 | 0,021993 | 0,0219922 | 0,022033 | 0,021986 | 0,02199 | 0,022055 | 0,021897 |
| 4270 | 2342 | 0,022316 | 0,0223228 | 0,022356 | 0,022326 | 0,022333 | 0,022367 | 0,022232 |
| 4266 | 2344 | 0,02233 | 0,0223342 | 0,022362 | 0,022345 | 0,022331 | 0,022375 | 0,022258 |
| 4263 | 2346 | 0,021983 | 0,0219904 | 0,021993 | 0,02201 | 0,021979 | 0,022023 | 0,021947 |
| 4259 | 2348 | 0,021309 | 0,0213088 | 0,021298 | 0,021331 | 0,021302 | 0,021335 | 0,021278 |
| 4255 | 2350 | 0,020391 | 0,0203998 | 0,020371 | 0,020434 | 0,020375 | 0,020412 | 0,020407 |
| 4244 | 2356 | 0,017684 | 0,0176596 | 0,017627 | 0,017695 | 0,017637 | 0,017653 | 0,017686 |
| 4219 | 2370 | 0,015586 | 0,01558 | 0,01553 | 0,015607 | 0,015596 | 0,015609 | 0,015558 |

TABLE 1.1-continued

Determination of the properties of a mixture of hydrocarbons for feeding to a steam cracker

| λ (cm-1) | Proximity Index Wavelengths λ (nm) | 1F measured | 1F estimated 3,80E-08 | 1A 8,94E-08 | 1B 9,30E-08 | 1C 1,87E-07 | 1D 2,84E-07 | 1E 3,57E-07 |
|---|---|---|---|---|---|---|---|---|
| 4212 | 2374 | 0,015581 | 0,0155792 | 0,015539 | 0,015612 | 0,015594 | 0,015601 | 0,015550 |
| 4191 | 2386 | 0,015644 | 0,0156246 | 0,015601 | 0,015661 | 0,015633 | 0,015606 | 0,015559 |
| 4181 | 2392 | 0,016231 | 0,0162086 | 0,016218 | 0,016204 | 0,016194 | 0,016263 | 0,016128 |
| 4174 | 2396 | 0,016428 | 0,016389 | 0,016395 | 0,016417 | 0,016355 | 0,016444 | 0,016334 |
| 4170 | 2398 | 0,016332 | 0,0162994 | 0,016317 | 0,016326 | 0,016250 | 0,016354 | 0,016250 |
| 4167 | 2400 | 0,016151 | 0,016113 | 0,016129 | 0,016135 | 0,016058 | 0,016171 | 0,016072 |
| 4160 | 2404 | 0,015691 | 0,0156668 | 0,015667 | 0,01569 | 0,015628 | 0,015714 | 0,015635 |
| 4149 | 2410 | 0,015467 | 0,0154834 | 0,015461 | 0,015505 | 0,015478 | 0,015525 | 0,015448 |
| 4139 | 2416 | 0,015865 | 0,0158868 | 0,015872 | 0,015906 | 0,015899 | 0,01593 | 0,015827 |
| 4136 | 2418 | 0,016018 | 0,0160316 | 0,016016 | 0,016058 | 0,016049 | 0,016079 | 0,015956 |
| 4132 | 2420 | 0,016145 | 0,0161568 | 0,016147 | 0,016185 | 0,016166 | 0,016203 | 0,016083 |
| 4122 | 2426 | 0,016501 | 0,0165196 | 0,016531 | 0,016545 | 0,016523 | 0,016578 | 0,016421 |
| 4115 | 2430 | 0,016816 | 0,0168624 | 0,016898 | 0,016889 | 0,016876 | 0,016929 | 0,01672 |
| 4108 | 2434 | 0,01718 | 0,017225 | 0,01725 | 0,017252 | 0,017266 | 0,017278 | 0,017079 |
| 4105 | 2436 | 0,017345 | 0,017372 | 0,017392 | 0,017409 | 0,017418 | 0,017412 | 0,017231 |
| 4102 | 2438 | 0,017449 | 0,01746 | 0,017503 | 0,017488 | 0,0175 | 0,017497 | 0,017312 |
| 4098 | 2440 | 0,017523 | 0,0175392 | 0,017563 | 0,017558 | 0,017579 | 0,017573 | 0,017423 |
| 4088 | 2446 | 0,01793 | 0,0178916 | 0,017915 | 0,017889 | 0,017922 | 0,01789 | 0,017842 |
| 4082 | 2450 | 0,018463 | 0,0184254 | 0,018443 | 0,018409 | 0,018448 | 0,0184 | 0,018427 |
| 4072 | 2456 | 0,019168 | 0,0191398 | 0,019162 | 0,019125 | 0,019123 | 0,019089 | 0,0192 |
| 4068 | 2458 | 0,019128 | 0,0190918 | 0,019147 | 0,019056 | 0,019049 | 0,019031 | 0,019176 |
| 4065 | 2460 | 0,018841 | 0,0188114 | 0,018879 | 0,018795 | 0,018753 | 0,018721 | 0,018909 |
| 4062 | 2462 | 0,01833 | 0,0183078 | 0,018377 | 0,018289 | 0,018246 | 0,018229 | 0,018398 |
| 4055 | 2466 | 0,016845 | 0,0168544 | 0,016868 | 0,016849 | 0,016804 | 0,016782 | 0,016969 |
| 4049 | 2470 | 0,015392 | 0,0153728 | 0,015367 | 0,015354 | 0,015347 | 0,015254 | 0,015542 |
| 4042 | 2474 | 0,014236 | 0,014211 | 0,014171 | 0,014203 | 0,014196 | 0,014095 | 0,01439 |
| 4032 | 2480 | 0,012938 | 0,0129096 | 0,012872 | 0,012905 | 0,012903 | 0,012826 | 0,013042 |
| 4026 | 2484 | 0,012416 | 0,0123958 | 0,012353 | 0,01242 | 0,012387 | 0,012354 | 0,012485 |
| 4016 | 2490 | 0,011841 | 0,0118108 | 0,011786 | 0,011821 | 0,011801 | 0,011787 | 0,011859 |
| 4010 | 2494 | 0,011216 | 0,0112028 | 0,011196 | 0,011209 | 0,011179 | 0,011198 | 0,011228 |
|  | Density | 0,7088 | 0,7081 | 0,7084 | 0,7081 | 0,7045 | 0,7071 | 0,7124 |
|  | CPC2 | 20,16 | 20,27 | 20,05 | 20,16 | 20,76 | 20,67 | 19,71 |
|  | LIN % | 34,37 | 35,15 | 34,33 | 34,62 | 36,42 | 36,7 | 33,69 |
|  | ISO % | 32,69 | 32,51 | 31,36 | 32,54 | 33,29 | 30,73 | 34,64 |
|  | NAPHT % | 25,69 | 25,00 | 26,86 | 25,66 | 23,79 | 26,21 | 22,49 |
|  | ARO % | 7,25 | 7,33 | 7,46 | 7,18 | 6,5 | 6,35 | 9,18 |
|  | IC | 108,8 | 107,9 | 109,7 | 109,2 | 105,1 | 105,3 | 110,3 |
|  | BENZ % | 1,05 | 1,06 | 1,22 | 1,06 | 0,93 | 1,06 | 1,07 |

In the Table 3.8 E-08 means $3.8 \times 10^{-8}$

Figure 1:
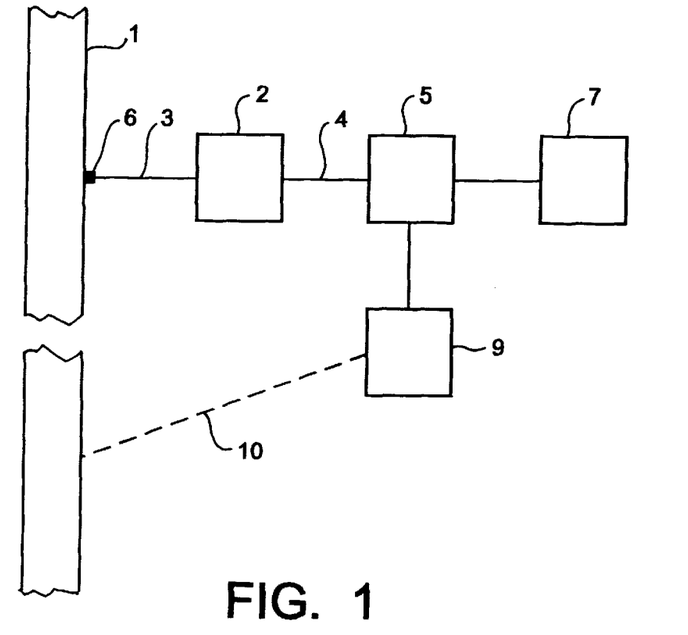
FIG. 1 represents a schematic diagram showing apparatus for use in the invention.

In FIG. 1, an optical fibre or tube 3 links a spectrometer 2 and a probe 6 in or at process line 1. The spectrophotometer 2 produces absorbance signals at more than 1 wavelength, which signals are passed via line 4 to computer 5, where the signals as such or after conversion to one or more derivative signals, are used to enable the computer to access the databank 7 of standard absorptions and properties/yields therein. The signals are compared to those of the standard absorptions as described above and one or more standard absorption(s) and its/their corresponding property(ies) or yield(s) The output of the computer 5 may be in the form of spectral absorbancies or a property or yield of the product in line 1 and may be printed in hard copy. Preferably however, the output as a signal is used to control the process involved with the product in line 1. ie for which line 1 is a feed or a product line; in this case the computer 5 is linked to and instructs the controller 9 which, via line 10, controls that process by acting on operating conditions eg. via valves/temperature and/or pressure controls in line 1 or in relation to line 1. By this means the property or yield of product in line 1 can be optimised.

Figure 2:
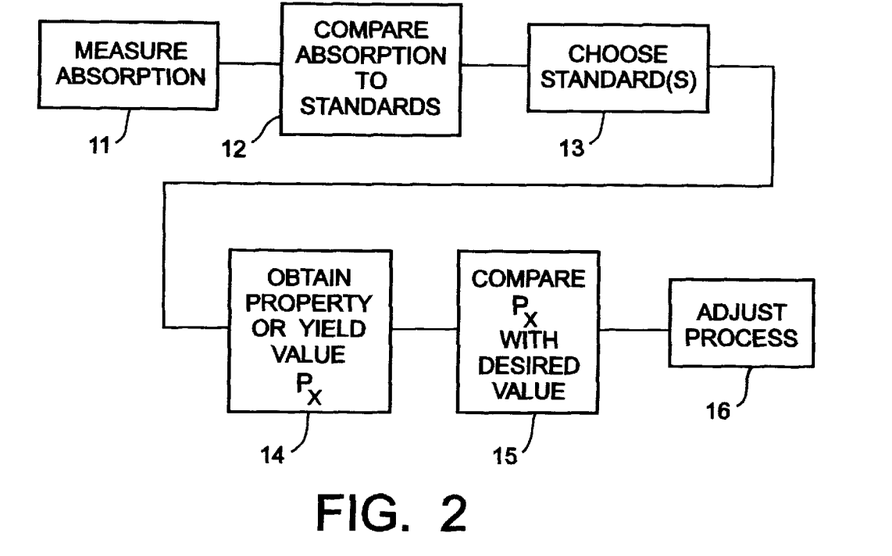
FIG. 2 represents a schematic block flow diagram for the method of the invention.

In FIG. 2, the initial operation 11 is to measure the absorption of the unknown, after which in the second step 12, the absorptions are compared to absorptions in spectra of standards, and in the third step 13, the spectra of the standard Sm are chosen according to criteria described above, and then in step 14, the property(ies) of the standard(s) Sm chosen is used to obtain the desired property or yield. If the spectrum of only 1 standard Sm is chosen, then the value $P_x$ of the unknown is the same as that of that standard Pm. If more than 1 spectrum is chosen, the value $P_x$ of the unknown is the average of the values Pm of the standards. If desired in an optional step 15, the value $P_x$ is compared to the desired value for the unknown and in step 16 the process involving the unknown is adjusted to make the value $P_x$ the same as the desired value.

We claim:

1. A method of determining or predicting a value $P_x$ of a property of a feed X to a steam cracking process or yield of said process, which method comprises measuring absorption $D_ix$ of said feed at more than one wavelength in the region 600–2600 nm, comparing said absorptions or a derivative thereof with absorptions $D_im$ or derivatives thereof at the same wavelengths for a number of standards S in a bank for which said property of yield P is known, and choosing from the bank at least one standard $S_m$ with property or yield $P_m$, said standard $S_m$ having the smallest average value of the absolute difference at each wavelength i between the absorption $D_ix$ or derivative thereof for the material and the absorption $D_im$ or derivative thereoffor the standard $S_m$ to obtain value $P_x$ which is the same as property or yield $P_m$ or an average of said properties or yields $P_m$ when more than one standard $S_m$ is chosen.

2. A method according to claim 1 wherein a proximity index is defined by $i^2(_{xm})=\Sigma(D_{ix}-D_{im})^2$, the proximity index being less than a minimal index $i_m$ which has been determined from preselected standards by (a) calculating for each pair of the standards a value of a corresponding proximity index to obtain a series of proximity indices with corresponding property differences, (b) relating values of the proximity indices to corresponding property differences, (c) calculating an average of the corresponding property differences for predetermined values L which are greater than a corresponding proximity index, (d) calculating the minimal index based on the average property differences and a reproducibility standard for the property.

3. A method according to claim 2 wherein the properties of the standards and spectra for consideration for possible choice are estimated by interpolation from measured properties of the standards and the spectra for which the proximity index with respect of an unknown is not more than 10 times the minimal index.

4. A method according to claim 1, wherein properties of synthetic standards, which are mixtures, and their spectra for consideration for possible choices for Sm are estimated from existing standards in the bank for which, in respect of each existing standard for use in said mixture equation (4) and (5) are met, $$MinCj-uj \leq C_j \leq Max\ Cj+uj \quad (4)$$

and $\Sigma\ Cij=1$ wherein Cj is fraction of component j in the sample i,
Min Cj is the minimum of j in the samples for which the method is to be used,
Max Cj is the maximum of j in the samples for which the method is to be used, and,
uj is between 1.0 and 0.05.

5. A method according to claim 4 wherein at least one of (i) the estimated Standards and the corresponding spectra, and (ii) the property $P_x$ of the unknown material and its spectrum, are added to the bank.

6. A method according to claim 1 wherein the property is a physicochemical property of feed X.

7. A method according to claim 1 wherein the property is a yield of a product of said process.

8. A method according to claim 1 which comprises determining from the absorptions of the feed to said process, the yield of at least one product from the process.

9. A method according to claim 8 which comprises determining the yield of at least one of alkene of 2–4 carbons, methane and coke as expressed by a cokability index.

10. A method according to claim 1 which comprises determining at least one property of said feed, which property is the percentage of at least one component thereof, its density and/or its mean molecular weight.

11. A method according to claim 1 which is computer implemented.

12. The method according to claim 1 which comprises determining at least one property of said feed.

13. A method according to claim 1 wherein a proximity index is defined by $i^2(_{xm})=\Sigma(D_{ix}-D_{im})^2$, the proximity index being less than a minimal index $i_m$ which has been determined from preselected standards by (a) calculating for each pair of the standards a value of a corresponding proximity index to obtain a series of proximity indices with corresponding property differences, (b) relating values of the proximity indices to corresponding property differences, (c) calculating an average of the corresponding property differences for predetermined values L which are greater than a corresponding proximity index, (d) calculating the minimal index based on the average property differences and a reproducibility standard for the property and wherein the property is a physicochemical property of feed X.

14. A method according to claim 1 wherein a proximity index is defined by $i^2(_{xm})=\Sigma(D_{ix}-D_{im})^2$, the proximity index being less than a minimal index $i_m$ which has been determined from preselected standards by (a) calculating for each pair of the standards a value of a corresponding proximity index to obtain a series of proximity indices with corresponding property differences, (b) relating values of the proximity indices to corresponding property differences, (c) calculating an average of the corresponding property differences for predetermined values L which are greater than a corresponding proximity index, (d) calculating the minimal index based on the average property differences and a reproducibility standard for the property and wherein the property is a yield of a product of said process.

15. A method according to claim 1 wherein a proximity index is defined by $i^2_{(xm)}=\Sigma(D_{ix}-D_{im})^2$, the proximity index being less than a minimal index $i_m$ which has been determined from preselected standards by (a) calculating for each pair of the standards a value of a corresponding proximity index to obtain a series of proximity indices with corresponding property differences, (b) relating values of the proximity indices to corresponding property differences, (c) calculating an average of the corresponding property differences for predetermined values L which are greater than a corresponding proximity index, (d) calculating the minimal index based on the average property differences and a reproducibility standard for the property and wherein the method comprises determining, from the absorptions of the feed to said process, the yield of at least one product from the process.

16. A method according to claim 1 wherein a proximity index is defined by $i^2_{(xm)}=\Sigma(D_{ix}-D_{im})^2$, the proximity index being less than a minimal index $i_m$ which has been determined from preselected standards by (a) calculating for each pair of the standards a value of a corresponding proximity index to obtain a series of proximity indices with corresponding property differences, (b) relating values of the proximity indices to corresponding property differences, (c) calculating an average of the corresponding property differences for predetermined values L which are greater than a corresponding proximity index, (d) calculating the minimal index based on the average property differences and a reproducibility standard for the property and wherein the method comprises determining at least one property of said feed, which property is the percentage of at least one component thereof, its density and/or its mean molecular weight.

17. A method according to claim 1 wherein the property is a physicochemical property of feed X and wherein the method comprises determining at least one property of said feed, which property is the percentage of at least one component thereof, its density and/or its mean molecular weight.

18. An apparatus suitable for use in the method of claim 1 which comprises an NIR spectrometer receiving at least one signal from a feed or product line in said process and being coupled to a computer to effect continuous measurement of the spectra of the feed and/or product and provide feed back control of the process.

19. A computer programmed to perform the method of determining or predicting a value $P_x$ of a property of a feed X to a steam cracking process or yield of said process, which method comprises measuring the absorption $D_{ix}$ of said material at more than one wavelength in the region 600–2600 nm, comparing said absorptions or a derivative thereof with absorptions $D_{im}$ or derivatives thereof at the same wavelength for a number of standards S in a bank for which said property or yield P is known, and choosing from the bank at least one standard $S_m$ with property $P_m$, said standard having the smallest average value of the absolute difference at each wavelength i between the absorption $D_ix$ or derivative thereof for the material and the absorption $D_im$ or derivative thereof for the standard $S_m$ to obtain $P_x$, which is the same as property or yield $P_m$ or an average of said properties or yields $P_m$ when more than one standard $S_m$ is chosen.

20. A computer implemented method for a system including a spectrometer linked to a process line containing a material X, which is a feed to a steam cracking process, a computer linked to the spectrometer, and a controller linked to the computer and the process line, the computer including databanks having stored therein absorptions of standard materials and corresponding properties of said materials, or yield of said process, the method comprises steps of:

measuring absorption at more than one wavelength in the region 600–2600 nm at the process line and producing absorption signals by the spectrometer in accordance therewith;

assessing the databanks of the computer in accordance with the absorption signals;

comparing, by the computer, the absorption signals to the absorptions of the standard materials stored in the databanks;

choosing at least one standard based on the comparing, said standard having the smallest average value of the absolute difference at each wavelength i between the absorption or derivative thereof for the material and the absorption or derivative thereof for the standards, to obtain a value which is the same as the corresponding property or yield or an average of said properties or yields when more than one standard is chosen; and controlling said process line in accordance with the choosing.

21. A computer programmed to perform the method of determining or predicting a value $P_x$ of a property of a feed X to a steam cracking process or yield of said process, which method comprises measuring the absorption $D_{ix}$ of said material at more than one n the region 600–2600 nm, comparing said absorptions or a derivative thereof with absorptions $D_{im}$ or derivatives thereof at the same wavelength for a number of standards S in a bank for which said property or yield P is known, and choosing from the bank at least one standard $S_m$ with property $P_m$, said standard having the smallest average value of the absolute difference at each wavelength i between the absorption $D_ix$ or derivative thereof for the material and the absorption $D_im$ or derivative thereof for the standard $S_m$ to obtain $P_x$, which is the same as property or yield $P_m$ or an average of said properties or yields $P_m$ when more than one standard $S_m$ is chosen, wherein a proximity index is defined by $i^2_{(xm)}=\Sigma(D_{ix}-D_{im})^2$, the proximity index being less than a minimal index $i_m$ which has been determined from preselected standards by (a) calculating for each pair of the standards a value of a corresponding proximity index to obtain a series of proximity indices with corresponding property differences, (b) relating values of the proximity indices to corresponding property differences, (c) calculating an average of the corresponding property differences for predetermined values L which are greater than a corresponding proximity index, (d) calculating the minimal index based on the average property differences and a reproducibility standard for the property.

22. A computer programmed to perform the method of determining or predicting a value $P_x$ of a property of a feed X to a steam cracking process or yield of said process, which method comprises measuring the absorption $D_{ix}$ of said material at more than one n the region 600–2600 nm, comparing said absorptions or a derivative thereof with absorptions $D_{im}$ or derivatives thereof at the same wavelength for a number of standards S in a bank for which said property or yield P is known, and choosing from the bank at least one standard $S_m$ with property $P_m$, said standard having the smallest average value of the absolute difference at each wavelength i between the absorption $D_ix$ or derivative thereof for the material and the absorption $D_im$ or derivative thereof for the standard $S_m$ to obtain $P_x$, which is the same as property or yield $P_m$ or an average of said properties or yields $P_m$ when more than one standard $S_m$ is chosen, wherein the property is a physicochemical property of feed X.

23. A computer programmed to perform the method of determining or predicting a value $P_x$ of a property of a feed X to a steam cracking process or yield of said process, which method comprises measuring the absorption $D_{ix}$ of said material at more than one wavelength in the region 600–2600 nm, comparing said absorptions or a derivative thereof with absorptions $D_{im}$ or derivatives thereof at the same wavelength for a number of standards S in a bank for which said property or yield P is known, and choosing from the bank at least one standard $S_m$ with property $P_m$, said standard having the smallest average value of the absolute difference at each wavelength i between the absorption $D_ix$ or derivative thereof for the material and the absorption $D_im$ or derivative thereof for the standard $S_m$ to obtain $P_x$, which is the same as Property or yield $P_m$ or an average of said properties or yields $P_m$ when more than one standard $S_m$ is chosen, wherein the property is a yield of a product of said process.

24. A computer programmed to perform the method of determining or predicting a value $P_x$ of a property of a feed X to a steam cracking process or yield of said process, which method comprises measuring the absorption $D_{ix}$ of said material at more than one wavelength in the region 600–2600 nm, comparing said absorptions or a derivative thereof with absorptions $D_{im}$ or derivatives thereof at the same wavelength for a number of standards S in a bank for which said property or yield P is known, and choosing from the bank at least one standard $S_m$ with property $P_m$, said standard having the smallest average value of the absolute difference at each wavelength i between the absorption $D_ix$ or derivative thereof for the material and the absorption $D_im$ or derivative thereof for the standard $S_m$ to obtain $P_x$, which is the same as property or yield $P_m$ or an average of said properties or yields $P_m$ when more than one standard $S_m$ is chosen, wherein the method comprises determining, from the absorptions of the feed to said process, the yield of at least one product from the process.

25. A computer programmed to perform the method of determining or predicting a value $P_x$ of a property of a feed X to a steam cracking process or yield of said process, which method comprises measuring the absorption $D_{ix}$ of said material at more than one wavelength in the region 600–2600 nm, comparing said absorptions or a derivative thereof with absorptions $D_{im}$ or derivatives thereof at the same wavelength for a number of standards S in a bank for which said property or yield P is known, and choosing from the bank at least one standard $S_m$ with property $P_m$, said standard having the smallest average value of the absolute difference at each wavelength i between the absorption $D_ix$ or derivative thereof for the material and the absorption $D_im$ or derivative thereof for the standard $S_m$ to obtain $P_x$, which is the same as property or yield $P_m$ or an average of said properties or yields $P_m$ when more than one standard $S_m$ is chosen, wherein the method comprises determining at least one property of said feed, which property is the percentage of at least one component thereof, its density and/or its mean molecular weight.

26. A computer implemented method for a system including a spectrometer linked to a process line containing a material X, which is a feed to a steam cracking process, a computer linked to the spectrometer, and a controller linked to the computer and the process line, the computer including databanks having stored therein absorptions of standard materials and corresponding properties of said materials, or yield of said process, the method comprises steps of:

measuring absorption at more than one wavelength in the region 600–2600 nm at the process line and producing absorption signals by the spectrometer in accordance therewith;

assessing the databanks of the computer in accordance with the absorption signals;

comparing, by the computer, the absorption signals to the absorptions of the standard materials stored in the databanks;

choosing at least one standard based on the comparing, said standard having the smallest average value of the absolute difference at each wavelength i between the absorption or derivative thereof for the material and the absorption or derivative thereof for the standards, to obtain a value which is the same as the corresponding property or yield or an average of said properties or yields when more than one standard is chosen; and controlling said process line in accordance with the choosing, wherein a proximity index is defined by $i^2(_{xm})=\Sigma(D_{ix}-D_{im})^2$, the proximity index being less than a minimal index $i_m$ which has been determined from preselected standards by (a) calculating for each pair of the standards a value of a corresponding proximity index to obtain a series of proximity indices with corresponding property differences, (b) relating values of the proximity indices to corresponding property differences, (c) calculating an average of the corresponding property differences for predetermined values L which are greater than a corresponding proximity index, (d) calculating the minimal index based on the average property differences and a reproducibility standard for the property.

27. A computer implemented method for a system including a spectrometer linked to a process line containing a material X, which is a feed to a steam cracking process, a computer linked to the spectrometer, and a controller linked to the computer and the process line, the computer including databanks having stored therein absorptions of standard materials and corresponding properties of said materials, or yield of said process, the method comprises steps of:

measuring absorption at more than one n the region 600–2600 nm at the process line and producing absorption signals by the spectrometer in accordance therewith;

assessing the databanks of the computer in accordance with the absorption signals;

comparing, by the computer, the absorption signals to the absorptions of the standard materials stored in the databanks;

choosing at least one standard based on the comparing, said standard having the smallest average value of the absolute difference at each wavelength i between the absorption or derivative thereof for the material and the absorption or derivative thereof for the standards, to obtain a value which is the same as the corresponding property or yield or an average of said properties or yields when more than one standard is chosen; and controlling said process line in accordance with the choosing, wherein the property is a physicochemical property of material X.

28. A computer implemented method for a system including a spectrometer linked to a process line containing a material X, which is a feed to a steam cracking process, a computer linked to the spectrometer, and a controller linked to the computer and the process line, the computer including databanks having stored therein absorptions of standard materials and corresponding properties of said materials, or yield of said process, the method comprises steps of:

measuring absorption at more than one n the region 600–2600 nm at the process line and producing absorption signals by the spectrometer in accordance therewith;

assessing the databanks of the computer in accordance with the absorption signals;

comparing, by the computer, the absorption signals to the absorptions of the standard materials stored in the databanks;

choosing at least one standard based on the comparing, said standard having the smallest average value of the absolute difference at each wavelength i between the absorption or derivative thereof for the material and the absorption or derivative thereof for the standards, to obtain a value which is the same as the corresponding property or yield or an average of said properties or yields when more than one standard is chosen; and controlling said process line in accordance with the choosing, wherein the property is a yield of a product of said process.

29. A computer implemented method for a system including a spectrometer linked to a process line containing a material X, which is a feed to a steam cracking process, a computer linked to the spectrometer, and a controller linked to the computer and the process line, the computer including databanks having stored therein absorptions of standard materials and corresponding properties of said materials, or yield of said process, the method comprises steps of:

measuring absorption at more than one wavelength in the region 600–2600 nm at the process line and producing absorption signals by the spectrometer in accordance therewith;

assessing the databanks of the computer in accordance with the absorption signals;

comparing, by the computer, the absorption signals to the absorptions of the standard materials stored in the databanks;

choosing at least one standard based on the comparing, said standard having the smallest average value of the absolute difference at each wavelength i between the absorption or derivative thereof for the material and the absorption or derivative thereof for the standards, to obtain a value which is the same as the corresponding property or yield or an average of said properties or yields when more than one standard is chosen;

controlling said process line in accordance with the choosing; and, determining, from the absorptions of the feed to said process, the yield of at least one product from the process.

30. A computer implemented method for a system including a spectrometer linked to a process line containing a material X, which is a feed to a steam cracking process, a computer linked to the spectrometer, and a controller linked to the computer and the process line, the computer including databanks having stored therein absorptions of standard materials and corresponding properties of said materials, or yield of said process, the method comprises steps of:

measuring absorption at more than one wavelength in the region 600–2600 nm at the process line and producing absorption signals by the spectrometer in accordance therewith;

assessing the databanks of the computer in accordance with the absorption signals;

comparing, by the computer, the absorption signals to the absorptions of the standard materials stored in the databanks;

choosing at least one standard based on the comparing, said standard having the smallest average value of the absolute difference at each wavelength i between the absorption or derivative thereof for the material and the absorption or derivative thereof for the standards, to obtain a value which is the same as the corresponding property or yield or an average of said properties or yields when more than one standard is chosen;

controlling said process line in accordance with the choosing; and, determining the yield of at least one of alkene of 2–4 carbons, methane and coke as expressed by a cokability index.

31. A computer implemented method for a system including a spectrometer linked to a process line containing a material X, which is a feed to a steam cracking process, a computer linked to the spectrometer, and a controller linked to the computer and the process line, the computer including databanks having stored therein absorptions of standard materials and corresponding properties of said materials, or yield of said process, the method comprises steps of:

measuring absorption at more than one wavelength in the region 600–2600 nm at the process line and producing absorption signals by the spectrometer in accordance therewith;

assessing the databanks of the computer in accordance with the absorption signals;

comparing, by the computer, the absorption signals to the absorptions of the standard materials stored in the databanks;

choosing at least one standard based on the comparing, said standard having the smallest average value of the absolute difference at each wavelength i between the absorption or derivative thereof for the material and the absorption or derivative thereof for the standards, to obtain a value which is the same as the corresponding property or yield or an average of said properties or yields when more than one standard is chosen;

controlling said process line in accordance with the choosing; and, determining at least one property of said feed, which property is the percentage of at least one component thereof, its density and/or its mean molecular weight.

32. A computer programmed to perform the method of determining or predicting a value $P_x$ of a property of a feed X to a steam cracking process or yield of said process, which method comprises measuring the absorption $D_{ix}$ of said material at more than one wavelength in the region 600–2600 nm, comparing said absorptions or a derivative thereof with absorptions $D_{im}$ or derivatives thereof at the same wavelength for a number of standards S in a bank for which said property or yield P is known, and choosing from the bank at least one standard $S_m$ with property $P_m$, said standard having the smallest average value of the absolute difference at each wavelength i between the absorption $D_ix$ or derivative thereof for the material and the absorption $D_im$ or derivative thereof for the standard $S_m$ to obtain $P_x$, which is the same as Property or yield $P_m$ or an average of said properties or yields $P_m$ when more than one standard $S_m$ is chosen, wherein the method comprises determining at least one property of said feed, which property is the percentage of at least one component thereof, its density and/or its mean molecular weight, wherein the property is a physicochemical property of feed X and wherein a proximity index is defined by $i^2(_{xm})=\Sigma(D_{ix}-D_{im})^2$, the proximity index being less than a minimal index $i_m$ which has been determined from preselected standards by (a) calculating for each pair of the standards a value of a corresponding proximity index to obtain a series of proximity indices with corresponding property differences, (b) relating values of the proximity indices to corresponding property differences, (c) calculating an average of the corresponding property differences for predetermined values L which are greater than a corresponding proximity index, (d) calculating the minimal index based on the average property differences and a reproducibility standard for the property.

33. A computer implemented method for a system including a spectrometer linked to a process line containing a material X, which is a feed to a steam cracking process, a computer linked to the spectrometer, and a controller linked to the computer and the process line, the computer including databanks having stored therein absorptions of standard materials and corresponding properties of said materials, or yield of said process, the method comprises steps of:

measuring absorption at more than one wavelength in the region 600–2600 nm at the process line and producing absorption signals by the spectrometer in accordance therewith;

assessing the databanks of the computer in accordance with the absorption signals;

comparing, by the computer, the absorption signals to the absorptions of the standard materials stored in the databanks;

choosing at least one standard based on the comparing, said standard having the smallest average value of the absolute difference at each wavelength i between the absorption or derivative thereof for the material and the absorption or derivative thereof for the standards, to obtain a value which is the same as the corresponding property or yield or an average of said properties or yields when more than one standard is chosen; and controlling said process line in accordance with the choosing; and, determining at least one property of said feed, which property is the percentage of at least one component thereof, its density and/or its mean molecular weight, wherein the property is a physicochemical property of material X, and wherein a proximity index is defined by $i^2(_{xm})=\Sigma(D_{ix}-D_{im})^2$, the proximity index being less than a minimal index $i_m$ which has been determined from preselected standards by (a) calculating for each pair of the standards a value of a corresponding proximity index to obtain a series of proximity indices with corresponding property differences, (b) relating values of the proximity indices to corresponding property differences, (c) calculating an average of the corresponding property differences for predetermined values L which are greater than a corresponding proximity index, (d) calculating the minimal index based on the average property differences and a reproducibility standard for the property.

34. A computer programmed to perform the method of determining or predicting a value $P_x$ of a property of a feed X to a steam cracking process or yield of said process, which method comprises measuring the absorption $D_{ix}$ of said material at more than one wavelength in the region 600–2600 nm, comparing said absorptions or a derivative thereof with absorptions $D_{im}$ or derivatives thereof at the same wavelength for a number of standards S in a bank for which said property or yield P is known, and choosing from the bank at least one standard $S_m$ with property $P_m$, said standard having the smallest average value of the absolute difference at each wavelength i between the absorption $D_ix$ or derivative thereof for the material and the absorption $D_im$ or derivative thereof for the standard $S_m$ to obtain $P_x$, which is the same as property or yield $P_m$ or an average of said properties or yields $P_m$ when more than one standard $S_m$ is chosen, wherein the method comprises determining the yield of at least one of alkene of 2–4 carbons, methane and coke as expressed by a cokability index, and determining from the absorptions of the feed to said process, the yield of at least one product from the process and, wherein a proximity index is defined by $i^2(_{xm})=\Sigma(D_{ix}-D_{im})^2$, the proximity index being less than a minimal index $i_m$ which has been determined from preselected standards by (a) calculating for each pair of the standards a value of a corresponding proximity index to obtain a series of proximity indices with corresponding property differences, (b) relating values of the proximity indices to corresponding property differences, (c) calculating an average of the corresponding property differences for predetermined values L which are greater than a corresponding proximity index, (d) calculating the minimal index based on the average property differences and a reproducibility standard for the property.

35. A computer implemented method for a system including a spectrometer linked to a process line containing a material X, which is a feed to a steam cracking process, a computer linked to the spectrometer, and a controller linked to the computer and the process line, the computer including databanks having stored therein absorptions of standard materials and corresponding properties of said materials, or yield of said process, the method comprises steps of:

measuring absorption at more than one wavelength in the region 600–2600 nm at the process line and producing absorption signals by the spectrometer in accordance therewith;

assessing the databanks of the computer in accordance with the absorption signals;

comparing, by the computer, the absorption signals to the absorptions of the standard materials stored in the databanks;

choosing at least one standard based on the comparing, said standard having the smallest average value of the absolute difference at each wavelength i between the absorption or derivative thereof for the material and the absorption or derivative thereof for the standards, to obtain a value which is the same as the corresponding property or yield or an average of said properties or yields when more than one standard is chosen;

controlling said process line in accordance with the choosing;

determining the yield of at least one of alkene of 2–4 carbons, methane and coke as expressed by a cokability index; and, determining from the absorptions of the feed to said process, the yield of at least one product from the process, wherein a proximity index is defined by $i^2_{(xm)} = \Sigma(D_{ix} - D_{im})^2$, the proximity index being less than a minimal index $i_m$ which has been determined from preselected standards by (a) calculating for each pair of the standards a value of a corresponding proximity index to obtain a series of proximity indices with corresponding property differences, (b) relating values of the proximity indices to corresponding property differences, (c) calculating an average of the corresponding property differences for predetermined values L which are greater than a corresponding proximity index, (d) calculating the minimal index based on the average property differences and a reproducibility standard for the property.

* * * * *

UNITED STATES PATENT AND TRADEMARK OFFICE
CERTIFICATE OF CORRECTION

PATENT NO. : 5,861,228
DATED      : January 19, 1999
INVENTOR(S) : Bernard Descales, et al.

It is certified that error appears in the above-identified patent and that said Letters Patent is hereby corrected as shown below:

On the title page, Item [30],
delete "[GB] United Kingdom" insert therefor: --[EPX] European Patent Office--.

Signed and Sealed this

Twenty-ninth Day of June, 1999

Attest:

Q. TODD DICKINSON

*Attesting Officer*   Acting Commissioner of Patents and Trademarks